United States Patent
Wanda et al.

(10) Patent No.: US 8,803,964 B2
(45) Date of Patent: Aug. 12, 2014

(54) IMAGING APPARATUS AND IMAGING METHOD, PROGRAM, AND RECORDING MEDIUM

(75) Inventors: Koichiro Wanda, Yokohama (JP); Akihiro Katayama, Zama (JP)

(73) Assignee: Canon Kabushiki Kaisha, Tokyo (JP)

(*) Notice: Subject to any disclaimer, the term of this patent is extended or adjusted under 35 U.S.C. 154(b) by 509 days.

(21) Appl. No.: 13/122,858

(22) PCT Filed: Nov. 26, 2009

(86) PCT No.: PCT/JP2009/070263
§ 371 (c)(1),
(2), (4) Date: Apr. 6, 2011

(87) PCT Pub. No.: WO2010/071024
PCT Pub. Date: Jun. 24, 2010

(65) Prior Publication Data
US 2011/0234785 A1  Sep. 29, 2011

(30) Foreign Application Priority Data
Dec. 18, 2008  (JP) ................................ 2008-322956

(51) Int. Cl.
*H04N 9/47* (2006.01)

(52) U.S. Cl.
USPC ........................................................... 348/78

(58) Field of Classification Search
None
See application file for complete search history.

(56) References Cited

U.S. PATENT DOCUMENTS

| | | | |
|---|---|---|---|
| 7,510,282 B2 | 3/2009 | Ueno et al. | |
| 7,566,128 B2 | 7/2009 | Tsukada et al. | |
| 7,641,338 B2 | 1/2010 | Fukuma et al. | |
| 2004/0114790 A1* | 6/2004 | Yamamoto et al. | 382/131 |
| 2006/0104477 A1* | 5/2006 | Isogai et al. | 382/100 |
| 2007/0070295 A1 | 3/2007 | Tsukada et al. | |
| 2007/0222946 A1 | 9/2007 | Fukuma et al. | |
| 2008/0024721 A1 | 1/2008 | Ueno et al. | |

(Continued)

FOREIGN PATENT DOCUMENTS

| | | |
|---|---|---|
| JP | 04-333972 A | 11/1992 |
| JP | 2001-291088 A | 10/2001 |

(Continued)

OTHER PUBLICATIONS

International Search Report and Written Opinion of the International Searching Authority mailed Feb. 16, 2010, in International Patent Application No. PCT/JP2009/070263.

*Primary Examiner* — Sath V Perungavoor
*Assistant Examiner* — Kate Luo
(74) *Attorney, Agent, or Firm* — Fitzpatrick, Cella, Harper & Scinto

(57) ABSTRACT

An imaging apparatus that captures an object that changes temporally includes: first acquisition means for acquiring an overview image of the object; determination means for determining a reference part in the overview image in which there is less temporal change than in other parts; setting means for setting, in a first overview image, a capturing position of the object where detailed capturing is to be performed; registering means for, in the case where a second overview image has been acquired for the same object as the object in the first overview image, registering the second overview image with the first overview image based on the reference parts in the first and second overview images; and second acquisition means for acquiring a detailed captured image of the object in a position corresponding to the capturing position of the first overview image in the registered second overview image.

14 Claims, 9 Drawing Sheets

(56) References Cited

U.S. PATENT DOCUMENTS

2008/0068033 A1* 3/2008 Kagami ................ 324/758
2008/0100612 A1* 5/2008 Dastmalchi et al. .......... 345/418
2008/0119727 A1* 5/2008 Barbagli et al. ............. 600/424
2008/0266249 A1* 10/2008 Allen et al. .................. 345/156
2011/0134392 A1 6/2011 Iwase et al.
2011/0137157 A1 6/2011 Imamura et al.

FOREIGN PATENT DOCUMENTS

| JP | 2002-140688 A | 5/2002 |
| JP | 2007-117714 A | 5/2007 |
| JP | 2007-252692 A | 10/2007 |
| JP | 2008-005987 A | 1/2008 |
| JP | 2008-029467 A | 2/2008 |

* cited by examiner

FIG. 7

| STATUS INFORMATION 701 | NON-EXTRACTION REGION 702 | NON-EXTRACTION REGION INFORMATION 703 | PRIORITY LEVEL 704 | REFERENCE POINT EXTRACTION METHOD 1 705 | REFERENCE POINT EXTRACTION METHOD 706 |
|---|---|---|---|---|---|
| ABNORMALITY IN MACULA RETINA | OVAL REGION INCLUDING MACULA RETINA | OVAL HAVING LENGTH OF MACULA RETINA +1 mm | A | BLOOD VESSEL WITHIN EXTRACTION REGION AND OPTIC NERVE PAPILLA SEGMENT | ... |
| ABNORMALITY IN OPTIC NERVE PAPILLA SEGMENT | OVAL REGION INCLUDING OPTIC NERVE PAPILLA SEGMENT | OVAL HAVING LENGTH OF MACULA RETINA +1 mm | A | BLOOD VESSEL WITHIN EXTRACTION REGION AND MACULA RETINA | ... |
| ... | ... | ... | ... | ... | ... |
| MACULA RETINA EDEMA | OVAL REGION INCLUDING MACULA RETINA | OVAL HAVING LENGTH OF MACULA RETINA +1 mm | A | BLOOD VESSEL WITHIN EXTRACTION REGION AND OPTIC NERVE PAPILLA SEGMENT | ... |
| ... | ... | ... | ... | ... | ... |
| ABNORMALITY IN UPPER-RIGHT REGION | UPPER-RIGHT REGION OF FUNDUS IMAGE | UPPER-RIGHT PORTION OF FOUR REGIONS INTO WHICH FUNDUS IMAGE IS DIVIDED | B | CLOSEST TO UPPER-LEFT, LOWER-RIGHT, AND LOWER-LEFT REGIONS | ... |
| ABNORMALITY IN SPECIFIED REGION | SPECIFIED REGION | REGION SPECIFIED THROUGH INPUT UNIT 3 | A | CHARACTERISTICS OUTSIDE OF SPECIFIED REGION | ... |
| ... | ... | ... | ... | ... | ... |

FIG. 8

| ORIGIN POINT X | ORIGIN POINT Y | END POINT X | END POINT Y | NUMBER OF IMAGES | ORIEN-TATION | INTERVAL | RESOLUTION · · · |
|---|---|---|---|---|---|---|---|
| 801 | 802 | 803 | 804 | 805 | 806 | 807 | 808 |

F I G. 11
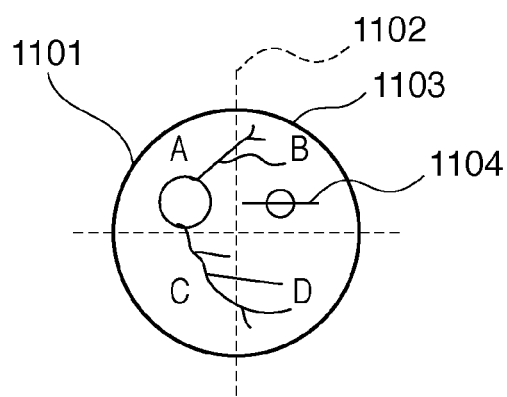

IMAGING APPARATUS AND IMAGING METHOD, PROGRAM, AND RECORDING MEDIUM

TECHNICAL FIELD

The present invention relates to an imaging apparatus and imaging method, a program, and a recording medium.

BACKGROUND ART

Ocular examinations have been garnering attention in recent years due to their effectiveness in the early diagnosis of various diseases, including lifestyle-related illnesses, leading causes of blindness, and so on. In such examinations, fundus cameras, ocular tomographic image acquisition apparatuses utilizing Optical Coherence Tomography (OCT), and so on used in ophthalmology clinics and the like are capable of objectively quantifying the scale of a disease's status. For this reason, such apparatuses are expected to be useful in making more precise disease diagnoses.

In typical OCT, the operator determines the capturing parameters of a cross-section image (for example, the part to be captured, the range to be captured, the level of detail, the proving method, and so on), and a cross-section image of a predetermined region of the eye is captured based on those capturing parameters. Because the cross-section image is an image showing a cross-section of only a narrow portion of the fundus segment, it is necessary to capture an extremely large number of cross-section images in order to observe the entire fundus. However, unlike examinations, the comparison of smaller numbers of images is suited to diagnoses of conditions of specific parts, post-operation follow-up observations, and so on, and therefore it is preferable to capture the same part even after time has passed.

Meanwhile, when observing changes in the status of the same part of the same patient, such as when observing the degree of progress of an eyeball condition or observing the effects of prescribed medicine or following up on an operation, it is necessary to capture cross-section images of the same part over a long period of time at specific intervals. Furthermore, comparing cross-section images of the same part that includes a lesion portion using fewer images of a wider range and a higher resolution is suited to comparisons of change over time.

With conventional technology such as, for example, early OCT apparatuses, it was not possible to specify the position of the cross-section image to be used in the diagnosis, and therefore multiple images were captured at a set interval within a specified proving region, and the cross-section images necessary for the diagnosis of the lesion were selected and used in the diagnosis. Recently, however, ophthalmologic imaging apparatuses provided with tracking mechanisms are being proposed; for example, specifications of a portion to be captured within a cross-sectional image are accepted from a user through a screen displaying images from a fundus camera, after which the cross-section images are captured. A configuration is also known in which cross-section images are captured using positional information in images of the fundus segment, anterior ocular segment, or the like captured using a fundus camera, a Scanning Laser Ophthalmoscope (SLO), or the like. These configurations are disclosed in the prior art documents that shall be discussed later.

Meanwhile, eyeballs experience movement in the line of sight even when in a focused state, which is known as visual fixation fine motion; it is thus difficult to fix the position of the eye of the subject to be examined. For this reason, it is difficult to stop on the same coordinates in the coordinate system of the apparatus and capture the eye, and therefore, in order to record the capturing position of the cross-section image, it is necessary to use the characteristics of the eye as a reference. However, the shape and characteristics themselves of an eyeball often temporally change, and temporal change caused by lesions frequently arises particularly in cases where diagnosis is necessary. Accordingly, it is difficult for the conventional technology to maintain the accuracy of positional information using the characteristics of the eye, and thus in situations where temporal change is expected and follow-up observation is necessary, the necessity of techniques for accurately capturing cross-section images of the same part is increasing.

Japanese Patent Laid-Open No. 2007-117714 discloses, as a technique for assisting an operator to capture a tomographic image, a configuration regarding a user interface for specifying, in a front image captured by a fundus camera, the capturing range of a cross-section image obtained through OCT. Furthermore, Japanese Patent Laid-Open No. 2008-029467 discloses a configuration regarding a user interface for specifying, in a wide-range image captured through SLO, the capturing range of a tomographic image obtained through OCT. According to the configurations disclosed in Japanese Patent Laid-Open Nos. 2007-117714 and 2008-029467, a user can specify the capturing range of a tomographic image while referring to the state of a front image of the fundus.

Meanwhile, Japanese Patent Laid-Open No. 2008-005987 discloses a configuration in which various pieces of setting information of the imaging apparatus are recorded for each cross-section image. Furthermore, Japanese Patent Laid-Open No. 2007-252692 discloses a configuration that records positional information of a fundus image and uses that information when capturing cross-section images.

Follow-up observation is widely carried out in medical fields in order to evaluate the progress of sicknesses, the effects of treatment, and so on. Such follow-up observation is carried out by performing multiple examinations over a long period of time, comparing the results of each examination, and making a diagnosis. In particular, in the diagnosis of ocular conditions, the task of acquiring images of the target part, such as a diseased part, and confirming temporal changes in the target part by comparing the images is executed frequently.

It is necessary to acquire images of the same part multiple times in order to perform such follow-up observations using images. However, in fundus examinations using conventional fundus observation apparatuses, it is difficult to acquire images of the same part. When acquiring images of the same part of the same patient on different examination dates, the position and orientation of the eyeball cannot be fixed in the same locations during capturing due to vision fixation fine motion and the like. For this reason, even if the control procedures, setting values, and so on of the imaging apparatus are the same, there is no guarantee that the same part can be captured.

Furthermore, in diagnoses using tomographic images of the fundus acquired through OCT, capturing cross-section images whose capturing range is large and whose resolution is high, and then making comparative observations using past cross-section images, is suited to diagnosis. However, capturing such cross-section images normally requires time, and thus it is difficult to obtain cross-section images of the same area suitable for such comparative observation using a method that continuously captures multiple images while shifting the proving region. Therefore, there is no guarantee that the same part as that in the past tomographic image capturing locations can be captured, and thus it has been necessary to capture a redundant number of images before the desired cross-section image can be obtained. Accordingly, such techniques have increased the burden of tasks performed by doctors, imaging technicians, and so on, due to increases in imaging operation times, selecting images from among the redundant captured images, performing additional imaging based on specifications from a doctor, and so on.

Furthermore, in the case of conditions that require diagnosis based on observations of temporal change, imaging is repeated over a long period of time; however, because the shapes and characteristics of eyeballs, ocular blood vessels, the compositions of diseased parts, and so on often change, there has been a problem in that the more a condition requires observations of temporal change, the more difficult it is to capture the same part. In other words, even if, for example, the imaging location of a cross-section image of an eye is recorded, the current shape and characteristics of the eye of that subject to be examined change; therefore, positional information based thereupon cannot correctly reproduce the past imaging positions.

DISCLOSURE OF INVENTION

The present invention has been conceived in light of the aforementioned problems, and aims to provide a technique for capturing a detailed image suitable for comparative observation of the same part of an object that experiences temporal change, accurately and with ease.

According to one aspect of the present invention, an imaging apparatus that captures an object that changes temporally includes: a first acquisition means for acquiring an overview image of the object; a determination means for determining a reference part in the overview image in which there is less temporal change than in other parts; a setting means for setting, in a first overview image, a capturing position of the object where detailed capturing is to be performed; a registering means for, in the case where a second overview image has been acquired for the same object as the object in the first overview image, registering the second overview image with the first overview image based on the reference parts in the first and second overview images; and a second acquisition means for acquiring a detailed captured image of the object in a position corresponding to the capturing position of the first overview image in the registered second overview image.

According to another aspect of the present invention, an imaging method for an imaging apparatus that captures an object that changes temporally includes the steps of: acquiring an overview image of the object; determining a reference part in the overview image in which there is less temporal change than in other parts; setting, in a first overview image, a capturing position of the object where detailed capturing is to be performed; registering, in the case where a second overview image has been acquired for the same object as the object in the first overview image, the second overview image with the first overview image based on the reference parts in the first and second overview images; and acquiring a detailed captured image of the object in a position corresponding to the capturing position of the first overview image in the registered second overview image.

Further features of the present invention will become apparent from the following description of exemplary embodiments (with reference to the attached drawings).

BRIEF DESCRIPTION OF DRAWINGS

FIG. 7 is a diagram illustrating an example of a table referred to by a control unit.

FIG. 8 is a diagram illustrating exemplary items of information recorded as capturing position information.

FIG. 11 is a diagram illustrating an example of a front image in a segmented state.

BEST MODE FOR CARRYING OUT THE INVENTION

Hereinafter, embodiments of the present invention shall be described in detail with reference to the appended drawings. Note that the constituent elements denoted in the following embodiments are only examples, and the scope of the present invention is not intended to be limited thereto. Furthermore, all combinations of the features described in the following embodiments are not necessarily required to achieve the present invention.

(Imaging Apparatus)

Figure 1:
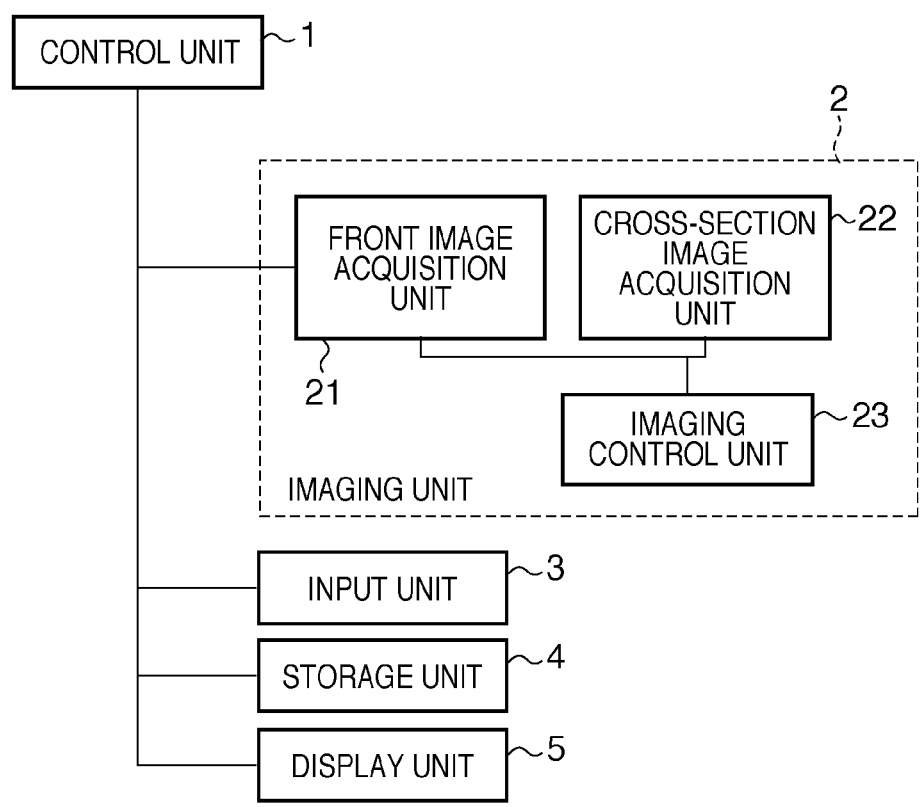
FIG. 1 is a diagram illustrating functional blocks of an imaging apparatus.

FIG. 1 is a diagram illustrating functional blocks of an imaging apparatus according to the present embodiment. The functional configuration of the imaging apparatus according to the present embodiment shall be described using FIG. 1.

A control unit 1 in FIG. 1 controls the imaging apparatus and the system as a whole, and performs control of image processes such as a reference determination process, which shall be described later. The control unit 1 can be realized by a common CPU (Central Processing Unit) or the like. An imaging unit 2 captures fundus images and cross-section images while tracking an eye to be examined, performing registering, and so on, and stores the captured images in an image memory.

An input unit 3 accepts operation/setting inputs of the imaging apparatus, inputs of status information (described later), and various operational inputs made by a user according to the present embodiment. The input unit 3 accepts operational inputs made using, for example, a numerical keypad, buttons, or the like provided in the imaging apparatus, or using a PC keyboard, pointing device, or the like. Furthermore, in addition to status information, front images, cross-section images, and positional information according to the present embodiment, the input unit 3 also accepts the input of files in which setting data and the like used in the operation of the imaging apparatus and the control of processing procedures have been saved, input from memories and through communication, and so on.

A storage unit 4 records fundus images and tomographic images captured by the imaging unit 2, status information, and various information related to imaging, such as positional information indicating the tomographic image capturing position within the fundus image. The storage unit 4 may be configured of a storage device within the imaging apparatus, such as, for example, a memory or a hard disk, a medium such as a DVD, or may be configured using a database such as a patient chart system.

A display unit 5 carries out displays necessary for an operator in accordance with the procedures of capturing processing (described later). For example, in addition to information related to the procedures of capturing processing and control information of the control unit 1, such as statuses of the imaging apparatus, processing statuses, and so on, the display unit 5 displays information related to the imaging unit 2, such as capturing parameters as well as front images, cross-section images, and information of the eye of the subject to be examined during imaging, and also displays images. The display unit 5 can be realized using a display device such as a liquid crystal panel, an organic EL panel, or the like. In addition, the display unit 5 can also display screens for input operations performed by the operator from whom the input unit 3 accepted input, and display information indicating the inputted details, operations status, and so on. Furthermore, the display unit 5 can also display saved images, setting information, and so on, such as past fundus images, tomographic images, status information, and positional information recorded in the storage unit 4.

(Imaging Unit)

The imaging unit 2 includes a front image acquisition unit 21, a cross-section image acquisition unit 22, and an imaging control unit 23. The imaging control unit 23 is a functional element that controls the operations of the front image acquisition unit 21 and the cross-section image acquisition unit 22. The front image acquisition unit 21 and the cross-section image acquisition unit 22 shall be described in detail hereinafter.

Front Image Acquisition Unit 21

Figure 2:
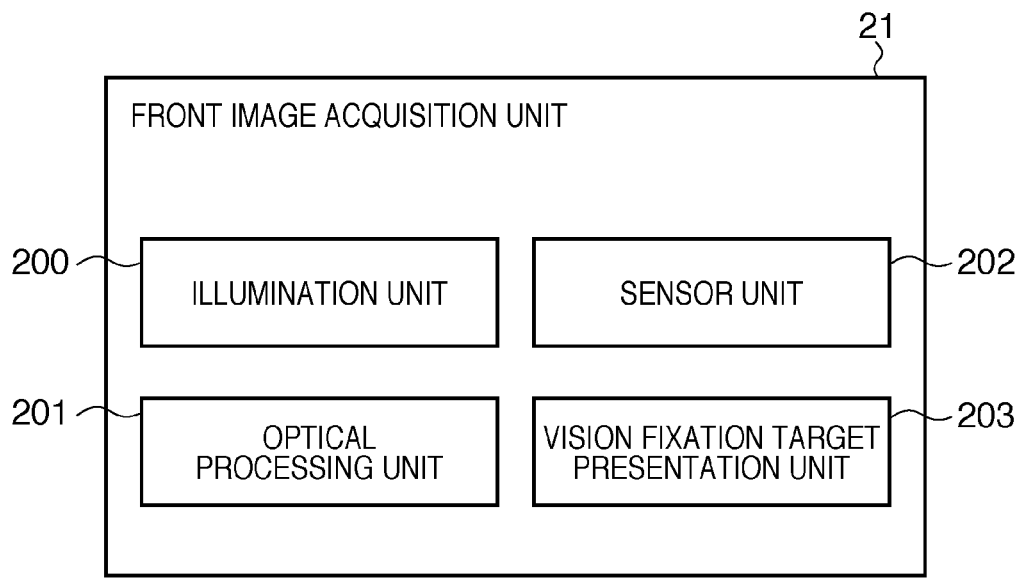
FIG. 2 is a block diagram illustrating an exemplary functional configuration of a front image acquisition unit.

The front image acquisition unit 21 is realized by a fundus camera, an SLO, or the like for acquiring a front image such as, for example, a fundus image or an anterior ocular segment image. The front image acquisition unit 21 functions as a first acquisition unit to acquire an overview image of an object. FIG. 2 is a block diagram illustrating an exemplary functional configuration in the case where the front image acquisition unit 21 is a fundus camera. The front image acquisition unit 21 is a device that captures and acquires a front image of an eye, and includes, for example, an illumination unit 200, an optical processing unit 201, a sensor unit 202, a vision fixation target presentation unit 203, and so on.

The illumination unit 200 includes an illumination system unit, such as a fundus illumination system unit, an anterior ocular segment illumination light source unit, or the like. The optical processing unit 201 is a functional element, provided with an optical system unit, that performs optical processing. Such an optical system unit includes, for example, an objective lens placed opposite the eye to be examined, a perforated mirror having imaging apertures in the hole portions, a focus lens that adjusts the focus by moving in the optical path direction, an imaging lens, a switching mirror that is located within the optical path during observation but that retracts from the optical path during imaging, and so on.

The sensor unit 202 includes an imaging sensor unit for capturing a fundus image, an observation sensor unit, and so on. The vision fixation target presentation unit 203 includes a liquid crystal element having multiple cells disposed in matrix form for displaying a vision fixation target, as well as a backlight, and the individual cells can be set to be transmissive or non-transmissive.

Next, an example of imaging operations in the front image acquisition unit 21 shall be described. First, the operator observes the anterior ocular segment, and generally registers the eye to be examined with the objective lens within the optical processing unit 201 by making operations through the input unit 3. In this state, the anterior ocular segment illumination light source in the illumination unit 200 is lit, and the illuminated anterior ocular segment image is controlled by the lenses and mirrors within the optical processing unit 201 to be formed upon the imaging surface of the observation sensor unit within the sensor unit 202. An anterior ocular segment image that has undergone photoelectric conversion within the observation sensor unit is then displayed in the display unit 5. In the case where the operator makes manual adjustments, he or she adjusts the position of the fundus camera relative to the eye to be examined by moving a stage in which the imaging unit 2 is provided while viewing the anterior ocular segment image, and then carries out the imaging.

Meanwhile, in the case where a fundus image is displayed, illumination from the fundus illumination system unit within the illumination unit 200 is reflected by the perforated mirror within the optical processing unit 201, passes through the pupil of the eye to be examined via the objective lens, and illuminates the fundus. The illuminated fundus image traverses the objective lenses, mirrors, and so on within the optical processing unit 201, and is formed upon the imaging surface of the observation sensor unit within the sensor unit 202. This formed image undergoes photoelectric conversion in the observation sensor unit, and a fundus image is then displayed in the display unit 5. Note that the operator can also adjust the position of the fundus camera relative to the eye to be examined by moving a stage in which the imaging unit 2 is provided while viewing the fundus image, and then carry out the imaging.

Cross-Section Image Acquisition Unit 22

Figure 3:
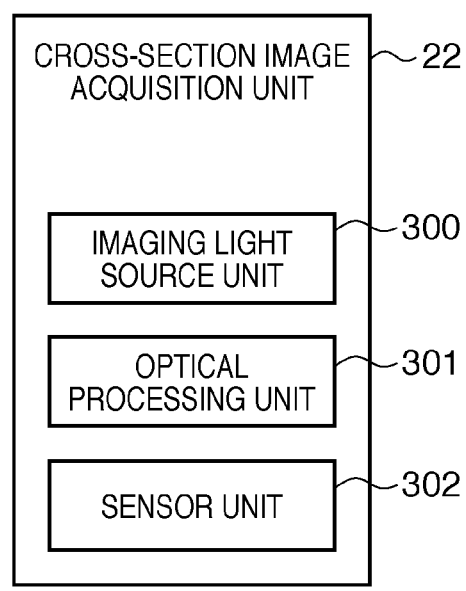
FIG. 3 is a block diagram illustrating an exemplary functional configuration of a cross-section image acquisition unit.

Next, the configuration of the cross-section image acquisition unit 22 shall be described with reference to FIG. 3. FIG. 3 is a block diagram illustrating an exemplary functional configuration of the cross-section image acquisition unit 22 as realized by an OCT apparatus.

The cross-section image acquisition unit 22 is a device that acquires a cross-section image such as an ocular tomographic image, and can be configured through, for example, time-domain OCT, Fourier-domain OCT, or the like. The cross-section image acquisition unit 22 functions as a second acquisition unit to acquire a detailed captured image of an object. The cross-section image acquisition unit 22 shown in FIG. 3 is an example of a functional configuration using time-domain OCT.

In FIG. 3, an imaging light source unit 300 is a light source for cross-section image capturing, such as, for example, an OCT apparatus low-coherence light source. An optical processing unit 301 is a functional element configured of an optical processing system unit group that performs optical processing, including a reference mirror, a galvanometer mirror, a mirror driving mechanism, and the like. A sensor unit 302 is a light-receiving element such as, for example, a CCD, and the control required by the various units is carried out by the imaging control unit 23.

Next, an example of the operational procedure for cross-section image acquisition using the cross-section image acquisition unit 22 shall be described. First, the operator makes inputs such setting parameters for imaging, and then, using the input unit 3, instructs a cross-section image to be captured. The "parameters for imaging" include, for example, parameters instructing the part from which the cross-section images to be acquired, the spatial range of the cross-section image, the resolution including the scan line interval, the proving method including the proving order and the proving direction, and so on. The imaging unit 2 is notified, via the control unit 1, of the settings and imaging instructions whose input was accepted by the imaging unit 3.

Under the control of the imaging control unit 23, the cross-section image acquisition unit 22 of the imaging unit 2 receives, using the light-receiving element of the sensor unit 302, light emitted from the low-coherence light source of the imaging light source unit 300 that has been reflected from the fundus segment of the eye to be examined, thereby capturing a cross-section image of the eye. After the imaging has ended, the acquired cross-section image is stored in a memory within the imaging control unit 23, and is then displayed in the display unit 5 via the control unit 1.

At this time, the imaging control unit 23 can, in response to a single imaging instruction from the input unit, acquire a single cross-section image, or can acquire multiple cross-section images based on the setting information. In addition, the imaging control unit 23 can also sequentially capture multiple cross-section images, sorting out images and determining the images to acquire.

Early fundus cameras generally employed a method whereby the operator moved a stage and captured images. OCT apparatuses also generally employed methods whereby capturing parameters were adjusted, the proving region was determined, and images were captured manually. However, in recent years, imaging apparatuses provided with functions for tracking the movement of the eyes using apparatuses such as the aforementioned characteristics of anterior ocular segment images and fundus images, image processing, and eye and line-of-sight detection sensors are being proposed. Although the present embodiment assumes that the imaging unit 2 is an imaging apparatus that has such tracking functionality, the imaging unit 2 may lack tracking functionality as well. As another example of the front image acquisition unit that is not a fundus camera, a Scanning Laser Ophthalmoscope (SLO), for example, may be used. Alternatively, the configuration may include both an SLO and a fundus camera.

In addition, the setting values such as the capturing parameters used by the imaging unit 2 do not necessarily need to be inputted by the operator; it is also possible for the imaging apparatus to automatically control the imaging. For example, imaging may be carried out using the initial setting values held within the cross-section image acquisition unit 22, or maybe carried out having set the depth direction of the cross-section image to an appropriate range through auto gain. Alternatively, a fundus image of a desired orientation can be captured by tracking the orientation or the like of the eye to be examined using a tracking mechanism, or a cross-section image in a specified position can be captured.

The setting values of such capturing parameters and the like can also be changed and the timing of imaging controlled by the imaging control unit 23, based on the individual information of the front image acquisition unit 21 and the cross-section image acquisition unit 22. In other words, it is possible to set the setting values used by the cross-section image acquisition unit 22 while using the information of the eye to be examined obtained by the front image acquisition unit 21, the tracking mechanism, and so on, and possible to control the timing of imaging. Conversely, it is also possible to change the settings of the front image acquisition unit 21, control imaging, and so on using the information of the cross-section image acquisition unit 22.

(Capturing Processing)

Figure 4:
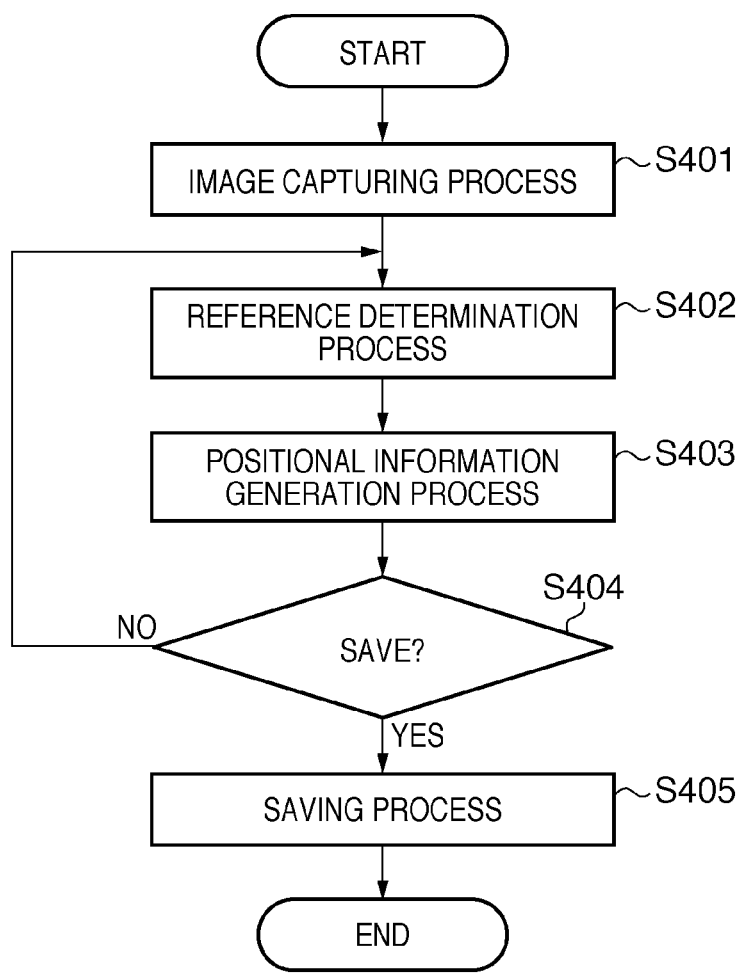
FIG. 4 is a flowchart illustrating the procedure of a capturing process.

FIG. 4 is a flowchart illustrating the procedure of a capturing process according to the present embodiment. The present embodiment describes a process for capturing a part to be used in the present diagnosis and that will also be necessary in future continuing follow-up observations, whereby it is necessary to repeatedly capture the same part, with accuracy, without experiencing the influence of lesions caused by temporal change. In particular, the present embodiment describes, with reference to FIG. 4, a case where there is an abnormality in the macula retina of an eyeball, and the shape and characteristics of the surrounding area of the macula retina change as a result of temporal change. Note that the front image acquired in the capturing process is an example of a first overview image (the first overview image).

The capturing process of the present embodiment commences when an instruction to capture the eye to be examined is inputted through the input unit 3. Each processing step in FIG. 4 is executed based on control performed by the CPU by which the control unit 1 is realized.

Image Capturing Process (S401)

In S401, a fundus image of the eye to be examined and a cross-section image through OCT are captured and displayed in the display unit 5 (an image capturing process). Although it is desirable for the fundus image of the eye to be examined and the cross-section image to be captured simultaneously, the capturing does not necessarily have to occur simultaneously as long as the capturing position of the cross-section image can be accurately associated with the fundus image. Alternatively, an SLO image may also be captured simultaneously with the cross-section image; the SLO image may then be registered with the fundus image captured by the fundus camera, and the capturing position of the cross-section image may be associated with the fundus image captured by the fundus camera.

Figure 5:
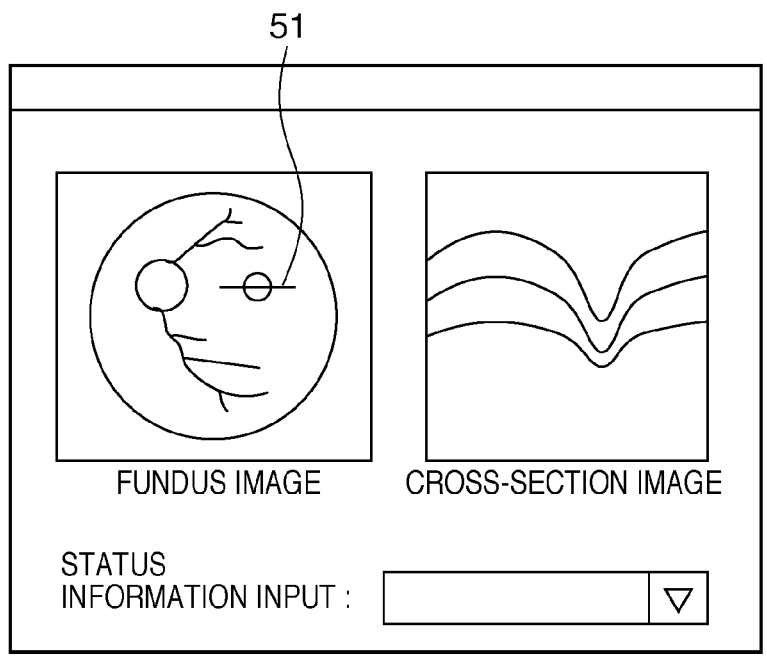
FIG. 5 is a schematic diagram illustrating an example of a screen displayed in a display unit.

Note that information of the capturing position of the cross-section image is recorded immediately following the capturing. This capturing position information may in this step be any positional information as long as that information is positional information that can be converted into positional information within the fundus image in later steps (for example, coordinate values of the operational position of the imaging apparatus). In this manner, the capturing position for an object for which detailed capturing is to be performed is set in an overview image (front image). The captured fundus image and cross-section image are displayed in the display unit 5 through, for example, a screen such as that shown in FIG. 5. FIG. 5 is a schematic diagram illustrating an example of the screen displayed in the display unit 5, including a fundus image, and a cross-section image, which is captured at a capturing position 51.

Reference Determination Process (S402)

Next, in S402, a reference determination process is performed. In the reference determination process (S402), a characteristic extraction region is determined (extraction region determination) so as to extract reference points for determining the capturing position of the cross-section image within the front image using status information (described later) inputted by the user. Then, using the characteristics within that extraction region, reference points to be used when generating the positional information of the cross-section image capturing position through a positional information generation process (S403; described later) are determined (reference point determination). Although the present embodiment describes a case where reference parts in the overview image (front image) whose temporal change is less than that of other parts are used as the points (reference points), it should be noted that lines, a region encompassing a set range, or the like may be used as the reference.

(1) Extraction Region Determination

The extraction region is a region in which the influence of lesions within the fundus image is expected to be low based on the status information. In the present embodiment, the extraction region is determined by first taking a region in which lesions are highly likely to be present within the fundus image region as a non-extraction region, and then taking the region within the fundus image region excluding the non-extraction region as the extraction region. The extraction region may, however, be specified manually.

The reference point determination process executed in S402 commences in response to the input, through the input unit 3, of information by which the operator can identify the status of the eye to be examined, or in other words, status information of the subject to be examined. Here, the status information is information indicating the status of the object. In the present embodiment, the object is a diseased part of the patient, and therefore, for example, disease names by which the condition of a specific part in a fundus image can be identified (example: macula retina edema), remarks indicating that there is an abnormality in a specific part, or the like can be used as the status information. Alternatively, the status information may be information, indicating the status of the subject, that makes it possible to specify regions in which temporal change is occurring or is expected to occur in a specific part of the subject. The status information may also be the degree of progress of the condition, the name of the diseased part, or the like.

Figure 6:
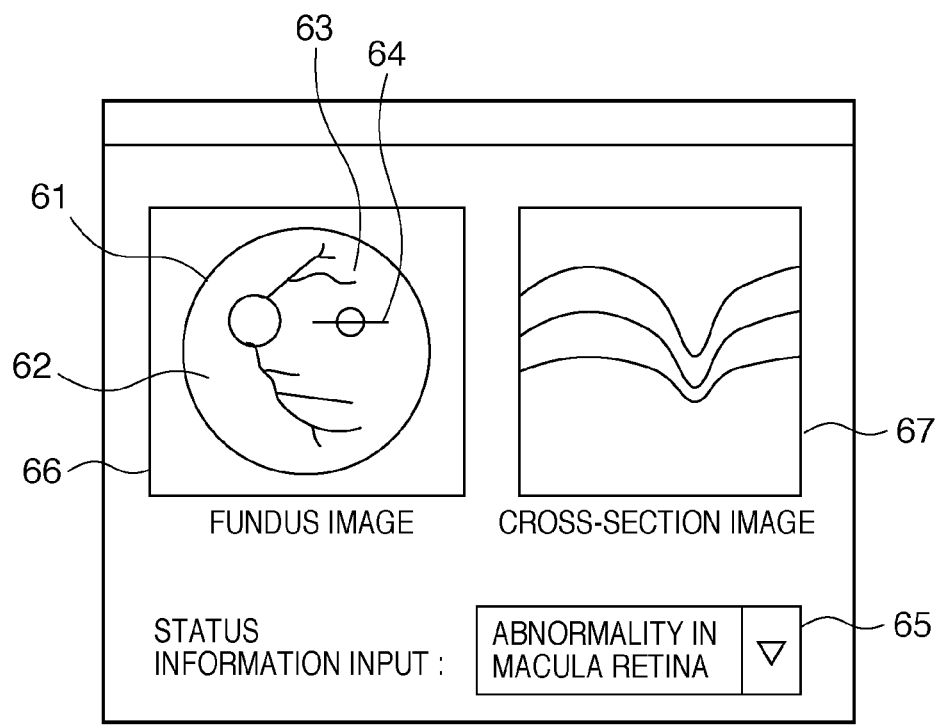
FIG. 6 is a diagram illustrating an example of a status information input screen.

In this manner, there is no particular restriction on the status information as long as it is information that makes it possible to identify the status of the subject. Furthermore, any method can be used to input the status information. The present embodiment describes an example in which points in which there are abnormalities in the macula retina are inputted as the reference points. In this case, the input of the status information can be realized through a method in which, for example, a user selects, from a screen displayed in the display unit 5, items prepared in advance in which there are abnormalities in the macula retina, and inputs those items. FIG. 6 is a diagram illustrating an example of such an input screen for status information.

FIG. 6 illustrates an example of an input screen for selecting the details of status information through a GUI (Graphical User Interface) (65). If the information can be identified by the control unit 1, the procedure of capturing processing according to the present embodiment can be applied. For example, passages of text may be inputted, or specific keywords such as disease names may be inputted; furthermore, multiple pieces of various status information may be inputted. In such a manner, status information specified by the user via the user interface can be inputted.

In the present embodiment, correspondence information indicating the correspondence between the status information indicating the status of the object and regions in which the temporal change is greater than other parts is stored as a reference table in a storage device. Then, when status information is inputted, a readout process for reading out the reference table is carried out, and the portions of the front image taken from the regions corresponding to the inputted status information are determined as the extraction region for extracting the reference parts. FIG. 7 is a diagram illustrating an example of the table referred to by the control unit 1. The information used by the imaging apparatus according to the present embodiment includes the registration of arbitrary keywords, priority levels of various pieces of status information, and rules for the case where multiple pieces of status information are applied and the like edited in advance by the operator; this information is registered as the reference table.

FIG. 7, 701 indicates the status information, in which information regarding the status of the diseased part is denoted. 702 indicates the non-extraction region, in which information of a region in which the possibility of a lesion is high and thus is not suitable for reference point extraction is denoted. 703 indicates non-extraction region information, in which information for identifying a non-extraction region is denoted. 704 indicates a priority level in which, in the case where there are multiple pieces of status information that enable methods for specifying non-extraction regions to be applied, priority levels at which the methods for specifying the non-extraction regions are to be applied are ranked using A, B, C, and so on. 705 and 706 indicate reference point extraction methods 1 and 2, in which methods for extracting reference points from extraction regions are denoted.

As illustrated in the example shown in FIG. 6, a fundus image 66 and a cross-section image 67 may be displayed in the status information input screen so that the operator can understand the non-extraction region. In FIG. 6, a fundus region 61 within the fundus image 66 is the region of the fundus within the fundus image. A non-extraction region 63 is a non-extraction region that has been calculated as a region from which references are not extracted. An extraction region 62 is a region obtained by excluding the non-extraction region 63 from the fundus region 61, and is a region from which characteristics to be used as reference points are extracted through the methods specified in the reference table illustrated in FIG. 7. In addition, a capturing position 64 is the capturing position of the cross-section image. In the present embodiment, a cross-section image 67 in the capturing position 64 is displayed in the GUI screen.

In the case where there is an abnormality in the macula retina, as in the present embodiment, the determination of the non-extraction region can be executed by extracting the macula retina from the fundus image, referring to the reference table held in advance by the control unit 1, and determining the region from which characteristics to be used as references are not to be extracted. As parameters, setting information, and so on necessary for determining the non-extraction region, information such as that in the reference table shown in the example in FIG. 7 may be held in advance by the control unit 1. Alternatively, the non-extraction region may be determined by the user specifying, for example, an arbitrary region through a GUI screen such as that shown in FIG. 5 using a pointing device or the like, and inputting the specified region as a non-extraction region.

Although it is desirable to display the non-extraction regions in a manner that enables those regions to be distinguished from the fundus image, the operator may specify an arbitrary color for the non-extraction region using the GUI, and color the region in such a manner. Furthermore, in the case where multiple non-extraction regions are simultaneously displayed, the case where priority levels differ for each region from which characteristics are to be extracted, and so on, those regions may be displayed using different colors.

Although in FIG. 6 in FIG. 7, the remaining region of the fundus image is determined as the extraction region after first determining the non-extraction region, note that the extraction region may be determined first. In other words, with respect to the reference table and the display screen, the example shown in FIG. 7 illustrates a case where the non-extraction region is handled. Meanwhile, FIG. 6 illustrates an example in which, when determining and displaying regions, the non-extraction region is determined first. However, in the present embodiment, the setting data in the reference table, the operations and display of the GUI, and so on are not limited to the non-extraction region; the extraction region can be handled in the same manner as well.

(2) Reference Point Determination

In the extraction of characteristics from an extraction region, various information, such as the macula retina within a fundus image, the center of a nerve papilla, the shape and branches of a blood vessel, and so on, can be extracted as the characteristics. As such characteristics, the maximum value, average value, median value, dispersion, standard deviation, number or percentage of points above a threshold, and so on of the luminance values of pixels can be extracted. Furthermore, the region may be divided into subregions, and the darkness, such as a darkness histogram, average darkness, darkness dispersion value, contrast, and so on may be extracted as the characteristics.

Hereinafter, one example of characteristic extraction shall be described, in which a region excluding the macula retina is taken as the extraction region, a blood vessel within a fundus image is extracted, and the branch point thereof is used as a reference. First, the region of the macula retina within the fundus image is determined as the non-extraction region. The region of the macula retina can be determined as a region encapsulated by pixels of a predetermined color range indicating the macula retina, a region containing pixels of a predetermined color range therewithin, or the like. Here, in the case where there are region candidates in multiple positions due to noise within the fundus image or the like, various methods can be used as methods to determine the region, such as employing both a user specification of a general area within the fundus image and determination based on pixel color. When the non-extraction region including the macula retina is determined, the extraction region is determined based on information on the region of the fundus image and the non-extraction region.

Next, pixels of a predetermined color range indicating a blood vessel are extracted from the extraction region. At this time, the color of healthier blood vessels that are resistant to temporal change are determined by a range using a predetermined threshold, and rather than extracting pixels of all colors indicating blood vessels, pixels indicating the color of the blood vessel to be extracted as a characteristic are extracted. Then, based on the branch point of the extracted blood vessel, the characteristics to be used as reference points can be determined using, for example, points on the border line between the nerve papilla and the blood vessel, the direction in which the blood vessel extends from the nerve papilla, what number branch point the branch point is, or another such rule. As long as the same method for selecting the characteristics can be used during both capturing and recapturing, any method may be employed.

When, for example, when two reference points have been determined, by using reference points determined in such a manner, a coordinate system is set within the fundus image, and the capturing position of the cross-section image is taken as the position in the coordinate system based on the reference points, thereby generating relative positional information. These characteristics can also be used in the registration between past fundus images and the fundus image of the eye to be examined in the procedure of the recapturing process in the present embodiment. Note that the reference determination process may be commenced automatically simultaneous to the end of status information input, or may be commenced in response to a specification to commence the reference determination process made through the input unit 3.

Positional Information Generation Process (S403)

In S403, a positional information generation process is executed, in which the capturing position of the cross-section image is converted into capturing position information in the fundus image based on the reference points determined in the reference determination process (S402) and positional information to be saved is generated. Here, the positional information can be information indicating the relative position with respect to the reference parts in the capturing position set in the front image. The capturing position information may be any positional information as long as it is positional information based on the reference points determined in S402. As an example thereof, an XY plane can be defined, extending orthogonally from one of the two reference points determined in S402, being orthogonal to a first line segment that passes through the two reference points, and the coordinate values of the origin and end points of the cross-section image capturing position can be recorded. In the case where multiple cross-section image capturing positions are to be enabled to be recorded, information such as the orientation and number of cross-section images, resolution indicating the number of pixels per unit length of the cross-section image, the slice interval for capturing, and so on may be added to the positional information, in addition to the aforementioned origin and end point coordinate values.

FIG. 8 is a diagram illustrating exemplary items of information recorded as capturing location information. In FIG. 8, 801 indicates the X coordinate of the origin point of the cross-section image capturing position, and 802 indicates the Y coordinate of the origin point of the cross-section image capturing position. 803, meanwhile, indicates the X coordinate of the end point of the cross-section image capturing position, and 804 indicates the Y coordinate of the end point of the cross-section image capturing position. 805 indicates the number of cross-section images to be captured, and 806 indicates the orientation of the cross-section image to be captured. 807 indicates the capturing position interval in the case where multiple cross-section images are to be captured at one time with a set interval provided therebetween, and 808 indicates the resolution of the cross-section image. For example, in the case where a single cross-section image is to be captured, the origin and end points make up the ends of a line segment specifying the position of the cross-section image. In the case where multiple cross-section images are to be captured with a set interval provided therebetween, the origin and end points indicate a rectangular region with 2 points at opposing corners of a rectangle that contains a group of multiple cross-section images, and the cross-section image capturing position can be specified by information such as the number of cross-section images 805 within that rectangular region or the capturing position interval 807.

Meanwhile, in order to simplify this capturing position information, information aside from the coordinate values shown in FIG. 8 may be prepared in advance within the control unit 1 as a rule regarding the capturing position of the imaging apparatus. In this case, the capturing position can be set with ease simply by adding an identifier that identifies that rule to the positional information to be saved.

Furthermore, there are cases where such capturing position rules are assigned to individual pieces of status information in advance. For example, there are cases where specific conditions are known in advance to occur in specific locations, and cases where the capturing position has already been determined according to the purposes of the examination. In such cases, assigning a capturing rule as one item in the reference table shown in FIG. 7 makes it possible to reduce the amount of information when generating the positional information, without requiring the coordinates of the capturing position to be denoted explicitly.

Acceptance of Saving Specification (S404)

When the positional information generation process (S403) ends, in S404, the operator checks whether or not it is acceptable to save that information, and specifies saving (holding) using the input unit 3. Here, in the case where the operator has not specified a save (NO in S404), it is possible to return to S402 and reexecute the process starting with the reference point determination process. When it is to be determined whether or not to use information regarding the capturing conditions, such as setting information, like that in the reference table of FIG. 7, that has been preset in the imaging apparatus in advance, existing setting information such as capturing rules, and so on as-is, that determination is carried out here. After the non-extraction region (or extraction region), reference points, positional information, and so on determined in S402 and S403 through the existing setting values and rules have been displayed in the display unit 5 and confirmed, the user carries out arbitrary region specifications and setting changes, and specifies the process to be carried out once again from S402.

Saving Process (S405)

In the case where the operator has specified saving through the input unit 3 in S404 (YES in S404), the procedure advances to S405, where a saving process is executed. In the saving process of S405, the fundus image captured in S401, the status information of the eye inputted in S402, and the positional information generated in S403 are associated with the cross-section image captured S401 and saved (held) in the storage unit 4. Here, with respect to the association with the cross-section image, any method may be used as long as that method allows the capturing position information of each cross-section image used in later diagnoses to be identified. For example, identifiers having the same value may be added to filenames, or the information may be collected and saved within folders created for each cross-section image.

In addition, the saving process of S405 may be carried out so that the information is stored in a device aside from a storage device such as the hard disk within the imaging apparatus, such as storing the information in the storage device of another computer via a network, writing the information to a recording medium such as a DVD-RAM, and so on. Furthermore, the configuration may be such that the information is registered as a single piece of data, in a database server, an electronic chart system, or the like. The various procedures of the capturing process according to the present embodiment are thus executed as described thus far.

(Recapturing Processing)

Figure 9:
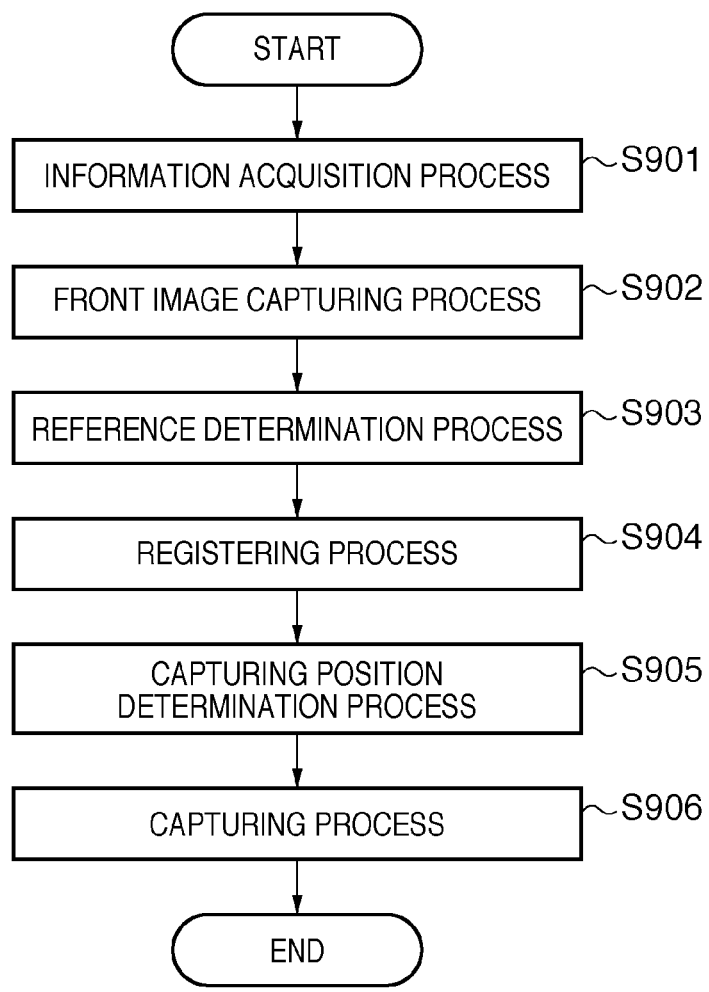
FIG. 9 is a flowchart illustrating the procedure of a recapturing process.

FIG. 9 is a flowchart illustrating the procedure of a recapturing process according to the present embodiment. The recapturing process is, for example, a capturing process that is carried out after a long period of time has elapsed following the execution of the capturing process according to the present embodiment, in order to confirm the degree of progress of the condition of the eye; this process is performed by acquiring a cross-section image of the same part so as to make a comparative diagnoses. The recapturing process of the present embodiment shall be described in detail with reference to FIG. 9. Note that the front image acquired in the recapturing process is an example of a second overview image (the second overview image).

Information Acquisition Process (S901)

Figure 10:
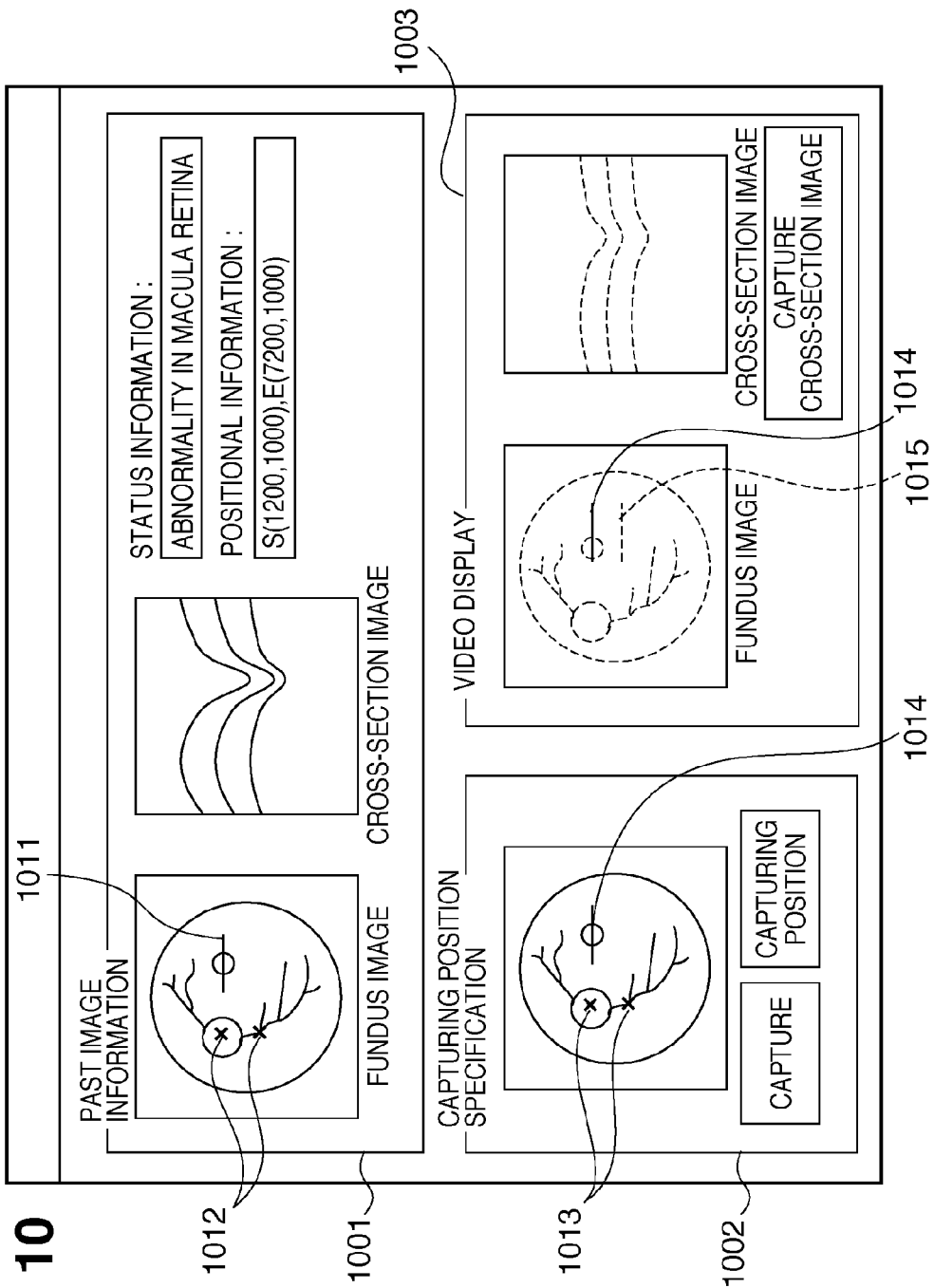
FIG. 10 is a diagram illustrating an example of a screen displayed in the case where acquired information is displayed.

First, in S901 of FIG. 9, the imaging apparatus according to the present embodiment acquires and displays information necessary for the recapturing process according to the present embodiment in response to an instruction from the operator via the input unit 3. A cross-section image and fundus image, status information, positional information, and so on for the same eye to be examined in the comparative diagnosis and used in the recapturing process is included in this information. The information can be acquired by, for example, reading out information stored in the storage unit 4, loading a file from a different medium instructed through the input unit 3, and so on. Note that when the sole purpose is simply capturing the same part, it is not absolutely necessary to load a cross-sectional image. In addition, although it is not absolutely necessary to display the information in the process of S901, the present embodiment describes, as an example, a case where information is displayed. FIG. 10 is a diagram illustrating an example of a screen displayed in the case where acquired information is displayed.

In FIG. 10, a past image information display portion 1001 is an example of a GUI screen that displays past cross-section images and fundus images, status information, and positional information. The past image information display portion 1001 executes displays related to the images, information, and so on loaded in S901, as well as past images and information calculated therefrom. In FIG. 10, the capturing position is indicated by 1011, and a reference point is indicated by 1012.

A capturing position specification portion 1002 is an example of a GUI screen in which a fundus image of the eye to be examined is displayed as a still image, and the capturing position of the cross-section image to be captured in the recapturing process is determined. In FIG. 10, a reference point is indicated by 1013, and the position specified for capturing is indicated by 1014.

An examined eye image display portion 1003 is an example of a screen in which the current eye to be examined is displayed as a moving picture. Although it is desirable for the displayed fundus image, cross-section image, and so on to be the same type of image as that used in the final diagnosis, the images may be different if used for supplementary applications in the cross-section image capturing process. The examined eye image display portion 1003 can be used for the operator to confirm the state of the eye to be examined during capturing preparations, used for capturing a fundus image for specifying the capturing position, and so on. In FIG. 10, the position of the currently-displayed cross-section image is indicated by 1015.

Front Image Capturing Process (S902)

When the loading of various images and information in the information acquisition process of S901 ends, in S902, a current fundus image of the eye to be examined is captured by the imaging unit 2, and the captured fundus image is displayed in the capturing position specification portion 1002 for specifying the cross-section image capturing position. The example of the fundus image in the capturing position specification portion 1002 in FIG. 10 indicates an exemplary image of the current eye to be examined in which the shape of the macula retina has changed due to a lesion. Note that this fundus image is captured with the same orientation as the fundus image loaded in S901 due to the tracking mechanism of the imaging unit 2. For example, the fundus image may be captured through an operational procedure in which the operator presses a capture button, for capturing a fundus image used to specify the capturing position within the capturing position specification portion 1002, while checking a fundus image video display screen as indicated by the examined eye image display portion 1003. In addition, fundus images may be captured sequentially in time series, and a fundus image for positional specification may then be selected from the multiple fundus images and displayed. When the front image capturing process ends, the procedure moves to the reference determination process of S903.

Reference Determination Process (S903)

The reference determination process of S903 is a process that calculates reference points in a past fundus image of the eye to be examined, and determines reference points in the current fundus image of the eye to be examined. In the reference determination process of S903, first, a reference determination process similar to the reference determination process in S402, executed in the capturing process of the past fundus image, is executed on the past fundus image loaded in S901, and the reference point 1012 is determined within the extraction region of the past fundus image. Note that in the case where reference points determined earlier for the past fundus image are stored within the storage device, that information may simply be read out.

Next, a reference determination process similar to S402 in the capturing process is executed on the current fundus image of the eye to be examined captured in S902. In other words, the reference table held by the control unit 1, an example of which is shown in FIG. 7, is referred to using the status information loaded in S901, and the reference point 1013 is determined in the current fundus image of the eye to be examined in an extraction region determined through a similar procedure as that used with the fundus image loaded within the current fundus image of the eye to be examined.

Registering Process (S904)

The registering process of S904 is a process that finds a relative positional attitude relationship between the coordinate system of the past fundus image of the eye to be examined inputted in S901 (a first region) and the coordinate system of the current fundus image of the eye to be examined captured in S902 (a second region). Here, the registering process is executed on two fundus images so that the reference points in the two fundus images of the eye to be examined, calculated in S903, match. The registering in this registering process may be executed using any method as long as it is a process that performs the registering of reference points based on characteristics extracted from an extraction region that has no temporal change. If the aforementioned first and second regions are within a two-dimensional image, the registering can be realized using two or more reference points, whereas if a similar method is to be executed for a three-dimensional region, the registering can be realized using three or more reference points. Although the present embodiment describes a case in which registering is performed with a two-dimensional fundus image, the embodiment is not limited thereto. For example, it is also possible to expand the same process to a three-dimensional region and execute the process using volumetric data created by capturing the fundus segment.

In this manner, in the case where a front image of an object for which a front image has been captured in the past is acquired, registering is executed based on the reference parts of the past front image and the reference parts of the newly-acquired front image. Note that the registering is executed by reading out a previous front image saved (held) in the storage device.

Capturing Position Determination Process (S905)

In the capturing position determination process of S905, a position corresponding to a previous capturing position in the front image registered in S904 is determined as the capturing position. To be more specific, the positional information in the previous fundus image loaded in S901 and registered through the registering process in S904 is converted into positional information in the current fundus image of the eye to be examined. The converted positional information is taken as the capturing position of the current cross-section image of the eye to be examined, and is displayed as a position specified to be captured within the fundus image, as indicated by the specified position 1014 in FIG. 10. Although the specified position 1014 indicates an example in which the position specified to be captured is displayed as a single line segment, it should be noted that the embodiment is not limited thereto. For example, in the case where multiple cross-section image capturing positions are to be displayed, multiple line segments may be displayed, or a rectangular region indicating the capturing region may be displayed along with the number of cross-section images captured at a set interval.

At this time, the specified position 1014 can be superimposed upon the fundus movie in the examined eye image display portion 1003 and displayed. Note that the specified position 1014 specifies a cross-section image capturing position to be used in diagnosis, and differs from the position of the cross-section image in the movie display in the examined eye image display portion 1003. For this reason, when displaying the capturing position of the cross-section image currently being displayed, it is necessary to carry out the display so that that information can be understood to be different positional information from the specified region 1014. An exemplary display of such cross-section image positional information is indicated by the currently-displayed cross-section image position 1015.

Capturing Process (S906)

The capturing process of S906 is a process that carries out capturing based on the capturing position information determined in S905. After the capturing position determination process of S905 ends, when, for example, the control unit 1 receives a capturing instruction from the input unit 3, such as an instruction resulting from the capture button shown in FIG. 10 being pressed, the control unit 1 instructs the imaging unit 2 to capture a cross-sectional image. If this is positional information specifying a capturing position within the current fundus image, the imaging unit 2 is automatically controlled so as to use the positional information as the capturing parameters of the apparatus control system, and a cross-section image of the specified position is captured.

As described thus far, in the present embodiment, in the case where a new front image has been acquired, this new front image is registered with a previous front image based on reference parts in a previous front image of the same object and reference parts in the newly-acquired front image. Then, a detailed captured image of the object is acquired from the position in the registered new front image that corresponds to a capturing position set in the previous front image. For this reason, even if the object has temporally changed, it is possible to acquire a detailed image through capturing over a long period of time by automatically tracking the same part.

In addition, in the present embodiment, a correspondence relationship between status information indicating the status of the object and regions in which the temporal change is greater than in other parts is stored in advance as a reference table, and portions of the front image from which regions corresponding to the inputted status information have been excluded are determined as reference parts. For this reason, the reference parts can be determined easily simply by the user inputting status information such as the disease name, the degree of progress of the condition, the name of the diseased part, remarks based on a diagnosis, and so on through a user interface.

As described thus far, according to the processing procedure of the present embodiment, a capturing position is determined by executing a registering process using reference parts extracted from regions that are not influenced by temporal change. For this reason, even in a case where the capturing dates are different and changes occur in the shape and characteristics near the macula retina due to temporal change, a cross-section image of the same part, accurately indicating the condition of the macula retina in detail for an easy comparison of the temporal change, can easily be captured without increasing redundant operations or a redundant number of captures.

Although the present embodiment describes an example of temporal change in which the characteristics of a fundus image change due to a change in the macula retina of an eyeball caused by a condition of the macula retina, it should be noted that any change can be used as the temporal change as long as it is a status change that occurs over time.

(Variation 1)

Although the aforementioned embodiment describes an example in which, in S402, regions aside from non-extraction regions within a fundus image region are determined as extraction regions for characteristics to be used as reference points in accordance with a non-extraction region calculation rule determined in advance based on status information, the invention is not limited thereto. For example, as indicated in a separate item in the reference table of FIG. 7, a fundus image region 2 may be recognized as four segmented regions (partial regions) in advance, the macula retina extracted from the fundus image, and regions that do not contain the macula retina, understood from the status information as having remarks, determined as extraction regions. FIG. 11 is a diagram illustrating an example of a front image in a segmented state. In the example of FIG. 11, the regions A, C, and D correspond to extraction regions, whereas B does not. In FIG. 11, a fundus image 1101 is segmented into four segmented regions 1103 by two segmentation lines 1102. A reference number 1104 represents a capturing position.

In addition, a priority rule may be given to the extraction regions. For example, in the case where the segmented region furthest from the region B that contains the macula retina is taken as the region from which to extract characteristics, due to that position being the most unlikely to be influenced by the macula retina and because the region B is a segmented region in which the possibility of temporal change is high, the region C may be taken as the only region from which to extract characteristics.

(Variation 2)

In addition, although the aforementioned embodiment describes an example in which the extraction regions of characteristics to be used as references are determined in S402 based on inputted status information, the invention is not limited thereto. For example, the reference point determination process of S402 may be executed based on regions specified by the operator via a GIU, rather than on the input of status information. To be more specific, the reference points may be determined based on regions with a low possibility of temporal change (characteristic extraction regions) or regions with a high possibility of temporal change (characteristic non-extraction regions) specified by the operator. In addition, a process for accepting selections of segmented regions, such as those indicated in Variation 1, presented by controlling the display of the display unit 5 from the user (operator) may be executed, and the extraction regions or reference parts may be determined based on the segmented regions whose selection was accepted. Furthermore, portions of the front image from which the partial regions whose selection has been accepted have been excluded may be determined as the reference parts. Such a configuration makes it possible for the user to set the reference parts with ease.

(Variation 3)

In addition, although the aforementioned embodiment describes an example of the capturing process in which the extraction regions of characteristics to be used as references are determined in the reference point determination process of S402 based on inputted status information, the invention is not limited thereto. For example, rather than the operator making inputs, the extraction regions of characteristics to be used as references may be determined using information of the cross-section image capturing position. For example, using the example of FIG. 11 referred to in Variation 1, assuming the capturing position to be a position with a high possibility of temporal change without extracting the macula retina, the segmented region B, which contains a capturing position, may thus be taken as a non-extraction region, and the control unit 1 may automatically determine the extraction regions through the same process as Variation 1.

(Variation 4)

In addition, in the reference point determination process of S402, extraction regions for characteristics to be used as reference points may be determined from regions generated using ANDs or ORs for extraction and non-extraction regions based on multiple pieces of status information. In addition, in the same manner, regions generated using ANDs or Ors may be determined as the extraction regions for characteristics, as for regions arbitrarily specified by the operator through the input unit 3 using information aside from the status information, regions automatically determined by the control unit 1, and so on.

(Variation 5)

In addition, although the aforementioned embodiment describes an example in which, in S905, the capturing position obtained by converting positional information of a past fundus image acquired in S901 and registered in S904 into positional information in the current fundus image of the eye to be examined is taken as the capturing position, the invention is not limited thereto. For example, corrections may be added by the operator prior to determining the final capturing position. For example, prior to the processing in S905 ending, a graphic object indicating a region such as a line segment, a rectangle, or the like representing the capturing position displayed in a GUI screen may be enabled to have its position, range, or the like altered through operations using a pointing device or the like.

(Variation 6)

In addition, although the aforementioned embodiment describes an example in which, in the capturing position determination process of S905, the current fundus image of the eye to be examined, the capturing position, and so on are displayed in a screen, this screen display is not absolutely necessary. For example, the capturing process of S906 may be executed without waiting for a capturing instruction, using the capturing position determined in S905 as-is.

(Variation 7)

In addition, although the aforementioned embodiment describes an example in which, in the capturing position determination process of S905, relative positional information in the current fundus image of the eye to be examined is generated, the invention is not limited thereto. For example, capturing position information converted directly into positional information indicated by a coordinate system of the imaging apparatus that can be associated with the coordinate system of the current front image of the eye to be examined may be used. In this case, the capturing process of S906 is executed using capturing position information in the apparatus coordinate system.

(Variation 8)

In addition, although the aforementioned embodiment describes an example in which the image to be processed is a fundus image of an eye, the image is not limited to the fundus, and the same method can be applied even if the image is a different front image, such as of the anterior ocular segment. Furthermore, although the above describes an exemplary configuration in which the references are points (reference points), the references may be reference lines, reference regions, or the like. In addition, it is also possible to execute registration whereby references are determined from a three-dimensional region such as volumetric data of the fundus segment reconstructed by capturing the fundus segment, rather than from a two-dimensional image such as a fundus image. Furthermore, although the aforementioned embodiment describes an exemplary configuration in which an image of one of the eyes is focused on as the eye to be examined, both eyes at the same subject to be examined, or multiple eyes of multiple subjects to be examined, may be handled.

(Other Embodiments)

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium).

As described thus far, according to the aforementioned configuration, it is possible to accurately capture a cross-section image of the same part even when capturing, over a long period of time, a cross-section image of the same part that experiences temporal change. In addition, because the amount of time spent on redundant tasks such as capturing comparative images suitable for follow-up observation, the generation of unnecessary multiple captured images, and the amount of time required for tasks such as selecting images suitable for diagnosis from among captured images and recapturing can be reduced, the above configuration also makes the capturing process more efficient.

According to the present invention, it is possible to provide a technique for capturing a detailed image suitable for comparative observation of the same part of an object that experiences temporal change, accurately and with ease.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-322956, filed on Dec. 18, 2008, which is hereby incorporated by reference herein in its entirety.

The invention claimed is:

1. An imaging apparatus that captures an object that changes temporally, the apparatus comprising:
   a first acquisition unit adapted to acquire a first overview image of the object;
   an input unit adapted to input lesion information of the object;
   a determination unit adapted to determine one or more reference points in a region, of the first overview image, in which there is less temporal change than in other regions by excluding, from the first overview image, a region corresponding to the lesion information inputted through the input unit, the region corresponding to the lesion information being a region in which the temporal change is greater than in other regions;
   a setting unit adapted to set, in the first overview image, a capturing position of the object where detailed capturing is to be performed;
   a registering unit adapted to register, in the case where a second overview image has been acquired for the same object as the object in the first overview image, the second overview image with the first overview image based on the one or more reference points in the first and second overview images; and
   a second acquisition unit adapted to acquire a detailed captured image of the object in a position corresponding to the capturing position of the first overview image in the registered second overview image.

2. The imaging apparatus according to claim 1, wherein the temporal change of the object is temporal change caused by a lesion.

3. The imaging apparatus according to claim 1, wherein the object is a diseased part of a patient, and
   wherein the lesion information contains at least one of a disease name, the degree of progress of the condition, the name of the diseased part, and remarks from a diagnosis.

4. The imaging apparatus according to claim 1, wherein the input unit inputs the lesion information specified by a user via a user interface.

5. The imaging apparatus according to claim 1, further comprising:
   a display control unit adapted to display the result of segmenting the first overview image into multiple partial regions in a display unit; and
   an accepting unit adapted to accept the selection of a partial region from a user,
   wherein the determination unit determines the reference point based on the partial region whose selection has been accepted by the accepting unit.

6. The imaging apparatus according to claim 5, wherein the determination unit determines a point obtained by excluding the partial region whose selection has been accepted by the accepting unit from the first overview image as the reference point.

7. The imaging apparatus according to claim 1, further comprising:
   a generation unit adapted to generate positional information indicating a relative position for the reference point in the capturing position set in the first overview image; and
   a holding unit adapted to hold the first overview image and the positional information in association with each other,
   wherein the registering unit reads out the first overview image from the holding unit and performs the registration, and
   wherein the second acquisition unit determines a position corresponding to the capturing position of the first overview image in the second overview image using the positional information, and obtains a detailed captured image of that position.

8. The imaging apparatus according to claim 1, wherein the first acquisition unit acquires a front image of the object as the first overview image of the object.

9. The imaging apparatus according to claim 8, wherein the object is a diseased eye of a patient, and
 wherein the front image is a front image of the fundus or the anterior ocular segment of the eye.

10. The imaging apparatus according to claim 9, wherein the second acquisition unit acquires a cross-section image of the eye as the detailed captured image of the object.

11. The imaging apparatus according to claim 10, wherein the first acquisition unit acquires the front image using a fundus camera, and
 wherein the second acquisition unit acquires the cross-section image using OCT.

12. An imaging method for an imaging apparatus that captures an object that changes temporally, the method comprising the steps of:
 acquiring a first overview image of the object;
 inputting lesion information of the object;
 determining one or more reference points in a region, of the first overview image, in which there is less temporal change than in other regions by excluding, from the first overview image, a region corresponding to the lesion information inputted at the step of inputting, the region corresponding to the lesion information being a region in which the temporal change is greater than in other regions;
 setting, in the first overview image, a capturing position of the object where detailed capturing is to be performed;
 registering, in the case where a second overview image has been acquired for the same object as the object in the first overview image, the second overview image with the first overview image based on the one or more reference points in the first and second overview images; and
 acquiring a detailed captured image of the object in a position corresponding to the capturing position of the first overview image in the registered second overview image.

13. A program stored on a non-transitory computer-readable recording medium that causes a computer to function as the imaging apparatus according to claim 1.

14. A non-transitory computer-readable recording medium on which is stored the program according to claim 13.

* * * * *